United States Patent [19]
Sill et al.

[11] 4,008,240
[45] Feb. 15, 1977

[54] XANTHENE AND THIOXANTHENE DERIVATIVES

[75] Inventors: Arthur D. Sill; Francis W. Sweet, both of Cincinnati, Ohio

[73] Assignee: Richardson-Merrell Inc., Wilton, Conn.

[22] Filed: Dec. 21, 1972

[21] Appl. No.: 317,148

[52] U.S. Cl. .................. 260/293.58; 260/246 B; 260/293.57; 260/326.5 SA; 260/326.5 CA; 260/328; 260/335; 424/248.51; 424/267; 424/274; 424/275; 424/283; 424/248.56; 424/248.57
[51] Int. Cl.² .................................. C07D 409/14
[58] Field of Search ...... 260/240 R, 246 B, 293.57, 260/293.58, 293.61, 293.62, 315, 326.85, 328, 335, 556 A, 570.5 P, 326.5 SA, 326.5 CA

[56] References Cited
UNITED STATES PATENTS

| | | | |
|---|---|---|---|
| 3,531,489 | 9/1970 | Albrecht et al. | 260/294.3 |
| 3,576,865 | 4/1971 | Fleming et al. | 260/559 |
| 3,592,819 | 7/1971 | Fleming et al. | 260/294.7 C |
| 3,647,860 | 3/1972 | Sill et al. | 260/475 FR |
| 3,701,786 | 10/1972 | Hopps et al. | 260/293.58 |
| 3,720,680 | 3/1973 | Albrecht et al. | 260/293.57 |

FOREIGN PATENTS OR APPLICATIONS

| | | |
|---|---|---|
| 776,535 | 12/1971 | Belgium |
| 5461 | 8/1971 | South Africa |

*Primary Examiner*—G. Thomas Todd
*Attorney, Agent, or Firm*—William J. Stein; George W. Rauchfuss, Jr.; Eugene O. Retter

[57] ABSTRACT

Novel 2,7-bis basic alkanol derivatives of xanthene and thioxanthene, their preparation and use for the prevention and inhibition of viral infections are disclosed.

5 Claims, No Drawings

XANTHENE AND THIOXANTHENE DERIVATIVES

FIELD OF THE INVENTION

This invention relates to new organic chemical compounds, to their preparation and to pharmaceutical compositions containing such compounds. The compounds described herein are antiviral agents which are useful in inactivating or inhibiting viruses by their administration to either an infected or a non-infected host.

BACKGROUND OF THE INVENTION

There is a growing body of information that viruses play a vital role in a broad range of diseases, some of which represent the most serious of man's ills. Arthritis, juvenile arthritis, diabetes, Hodgkin's disease and various immunological diseases and degenerative diseases of the central nervous system have been linked to viruses as the causative agents.

At present, the control of virus infections is primarily achieved by means of immunization vaccines. For example, poliomyelitis, smallpox, measles and influenza are well recognized diseases in which virus vaccines have proven effective. In general, however, virus vaccines have had only a moderate success in animal prophylaxis. Each vaccine acts primarily against a specific virus and is not heterophilic in the protection it offers. Hence, vaccines have not provided a practical solution against the wide array of infectious viruses, even where limited, as for example, to respiratory viruses alone.

One approach to the control of virus-related diseases and, particularly to the spread of such virus diseases, has been to search for medicinal agents or chemotherapeutic agents which are capable of inhibiting the growth of viruses, thereby preventing the spread of disease as well as preventing further spread and damage to cells and tissues of the animal host which have not as yet been infected. Heretofore, only a limited number of virus infections such as smallpox, Asian influenza and herpes keratitis have been prevented by chemical antiviral agents. Sulfonamides and antibiotics which have revolutionized the treatment of bacterial infections have substantially no effect upon virus infections. Certain infections caused by large viruses, such as lymphogranuloma venereum, psittacosis and trachoma have been successfully treated using antibiotics and sulfa drugs. However, the majority of infections have not been responsive to attack by chemotherapeutic agents. Thus, it can be seen that there is a need for new chemotherapeutic agents which are effective against a broad range of virus diseases, and which at the same time, are non-toxic to the host.

As a result of a long series of investigations, applicants have discovered a novel class of 2,7-bis basic alkanol derivatives of xanthene and thioxanthene which are particularly useful antiviral agents. These compounds are effective against a wide spectrum of virus infections and are useful in treating such infections both prophylactically and therapeutically. Additionally, these compounds further serve as valuable intermediates for the preparation of 2,7-bis basic vinylene derivatives of xanthene and thioxanthene, which are also useful as anti-viral agents.

Copending applications, Ser. No. 97,379, filed Dec. 11, 1970, now U.S. Pat. No. 3,859,286 and Ser. No. 137,055, filed Apr. 23, 1971, now U.S. Pat. No. 3,856,789, represent the closest art known to applicants and disclose bis basic ketones of xanthene and thioxanthene having antiviral activity. The compounds of the present invention differ from those of the prior art in that they are not bis basic ketones, but rather represent bis basic α-alkanols of xanthene and thioxanthene. Additionally, certain of the preferred 2,7-isomers previously described are useful as starting materials in the preparation of the compounds of the present invention. To applicants' knowledge the compounds described and claimed herein are novel compounds which have not previously been described nor reported in the literature. Furthermore, no bis basic α-alkanols of any type are known which have previously been reported to possess antiviral activity. The instant compounds demonstrate a wide spectrum of antiviral activity in varying degrees which could not have been predicted from a knowledge of the present state of the art.

SUMMARY OF THE INVENTION

This invention relates to new derivatives of xanthene and thioxanthene, to their preparation and to their use as pharmaceutical agents. More particularly, the compounds of the present invention are 2,7-bis basic alkanol derivatives of xanthene and thioxanthene which are useful as antiviral agents. Still more particularly, the compounds of the present invention may be represented by the following general formula:

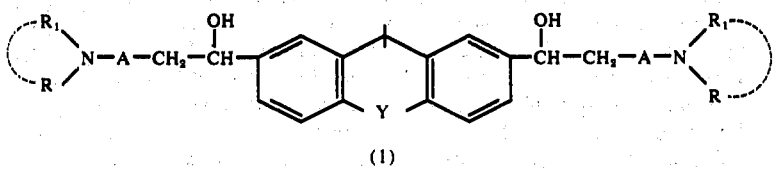

(1)

wherein Y is oxygen or sulfur; A is a straight or branched alkylene chain having from 1 to 4 carbon atoms; R and $R_1$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than in the 1-position of the alkenyl group, and when R and $R_1$ are taken together with the nitrogen atom to which they are attached represent the pyrrolidinyl, morpholino or piperidino radical; and their pharmaceutically acceptable acid addition salts.

The 2,7-bis basic alkanol derivatives of xanthene and thioxanthene (1) are prepared by the sodium borohydride reduction of the corresponding 2,7-bis basic ketones of xanthene and thioxanthene (II) as illustrated in the following reaction scheme:

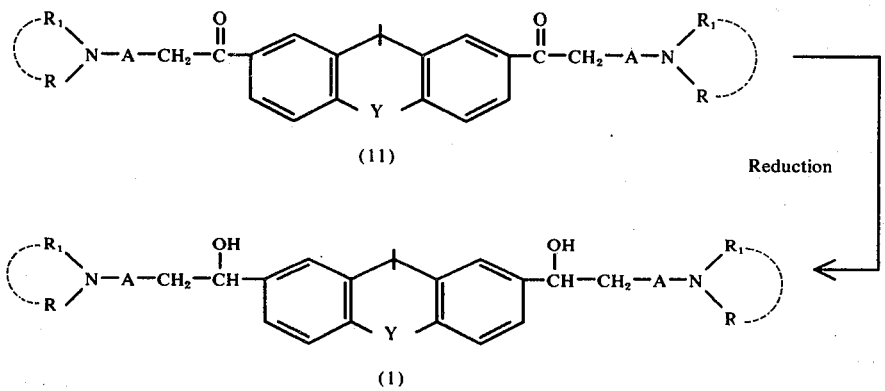

(II)

Reduction (I)

In the above reaction, the symbols A, R and R₁ and Y have the values previously assigned to them.

To achieve an antiviral effect the compounds of this invention are administered to a suitable host using a variety of compositions. Such compositions may be administered either prior to infection, as with a prophylactic use or treatment, or they may be therapeutically administered subsequent to infection, as with a curative use or treatment. The compounds of this invention may also be applied externally or topically directly at the situs of infection, or they may be administered internally or systemically, irrespective of whether the treatment is prophylactic or curative in nature. In either event, replication of the virus is inhibited or prevented with the concomitant result that the various disease symptoms characteristic of the pathogenic virus infection are no longer present.

DETAILED DESCRIPTION OF THE INVENTION

As can be seen from general formula (I) above, there are two basic side chains, each of which is separately located on a benzenoid portion of the xanthene or thioxanthene nucleus. Additionally, each side chain can be viewed as consisting essentially of a basic amino function located at the terminal end of the side chain, a secondary alkanol located at its proximal end which serves as a bridging function, and an alkylene chain of determinate length which separates the bridging function from the terminal basic amino function.

The alkylene chain separating the amino function from the tricyclic ring consists of from 1 to 4 carbon atoms and represents either a straight or branched alkylene chain. Additionally, each of the alkylene groups may be the same or different; preferably, however, both alkylene groups are the same. Illustrative of the various alkylene groups which are represented by the symbol A are methylene, ethylene, trimethylene, 1-methylethylene, tetramethylene and 2-methyltrimethylene.

The basic amino function represented by the symbol

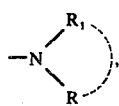

can be a primary, secondary or a tertiary amino group. Preferably, each amino group is a tertiary amine. The symbols R and R₁ represent either hydrogen or a lower alkyl group. The term lower alkyl as used herein with regard to the basic amino function relates to groups having from 1 to 6 carbon atoms. Illustrative of such groups can be mentioned both straight or branched chain alkyl radicals such as: methyl, ethyl, n-propyl, isopropyl, n-butyl, sec-butyl, isoamyl, n-pentyl and n-hexyl. When R and R₁ each represent lower alkyl, a preferred subgenus is formed.

Each R and R₁ can also represent a cycloalkyl group having from 3 to 6 carbon atoms. Illustrative of such groups are the cyclopropyl, cyclobutyl, cyclopentyl and cyclohexyl radicals.

The symbols R and R₁ also represent an alkenyl group having from 3 to 6 carbon atoms. In addition to the unsaturation which must be present, this unsaturation must be in a position other than the 1-position of the alkenyl group in order to prevent hydrolysis from occurring. Illustrative of such groups are the allyl, 3-butenyl and the 4-hexenyl radicals.

R and R₁ may also be joined with the nitrogen atom to which they are attached to represent various saturated monocyclic, heterocyclic radicals. Typical of such heterocyclic groups are the 1-pyrrolidinyl, piperidino or morpholino radicals. Compounds containing these groups are readily prepared and typify saturated monocyclic, heterocyclic radicals which are generally useful in lieu of the dilower alkylamino groups present in the compounds of this invention.

The alkanol portion of the molecule serves as a bridging function which anchors the basic alkylene side chain to the aromatic nucleus. Thus, the alkanols of the present invention are characterized by the fact that they are all secondary alcohols which must be located in an α-position with respect to the aromatic nucleus. The aromatic nucleus consists of either xanthene or thioxanthene depending upon whether the symbol Y is either oxygen or sulfur. In either event substitution of the bis basic side chains takes place only in the 2 and 7-positions of the xanthene or thioxanthene nucleus.

Illustrative of specific basic compounds of the present invention represented by general formula (I) are: α,α-bis[3-(diethylamino)propyl]xanthene-2,7-dimethanol, α,α′-bis(3-piperidinopropyl)xanthene-2,7-dimethanol, α,α′-bis[2-(N-cyclohexyl-N-methylamino)ethyl]xanthene-2,7-dimethanol, α,α′-bis[4-(diallylamino)butyl]xanthene-2,7-dimethanol, α,α′-bis[3-(diisopropylamino)propyl]xanthene-2,7dimethanol, α,α′-bis[2-(diisoamylamino)ethyl]xanthene-2,7-dimethanol, α,α′-bis[5-(cyclohexylamino)-2-methylpentyl]xanthene-2,7-dimethanol, α,α′-bis[3-(dimethylamino)propyl]thioxanthene-2,7- dimethanol, α,α'-bis(4-piperidinobutyl)thioxanthene-2,7-dimethanol, α,α'-bis[2-(1-pyrrolidinyl)ethyl]thioxanthene-2,7-dimethanol, α,α'-bis[3-(N-cyclohexyl-N-methylamino)propyl]thioxanthene-2,7-dimethanol, α,α'-bis[3-(diisopropylamino)propyl]thioxanthene-2,7-dimethanol and α,α'-bis[3-(diethylamino)-1-methylpropyl]thioxanthene-2,7-dimethanol.

The expression "pharmaceutically acceptable acid addition salts" encompasses any non-toxic organic or inorganic acid addition salts of the base compounds represented by formula (I). Illustrative inorganic acids which form suitable salts include hydrochloric, hydrobromic, sulfuric and phosphoric acids and acid metal salts such as sodium monohydrogen orthophosphate and potassium hydrogen sulfate. Illustrative organic acids which form suitable salts include the mono, di and tricarboxylic acids, for example, acetic, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methane sulfonic acid and 2-hydroxyethane sulfonic acid. Either the mono or the di-acid salts can be formed, and such salts can exist in either a hydrated or a substantially anhydrous form.

The 2,7-bis basic ketones of xanthene and thioxanthene (II) which serve as starting materals for the compounds of the present invention are obtained via a two-step process. The first step involves a Friedel-Crafts acylation of xanthene and thioxanthene to form the corresponding 2,7-bis(ω-haloalkanoyl) derivatives. These derivatives can then be aminated under a variety of conditions to form the 2,7-bis basic ketones of xanthene and thioxanthene. For example, the ω-haloalkanoyl derivatives can be heated with a large excess of amine, the excess amine serving as both reaction medium and hydrohalide acceptor. Alternatively, the compounds may be heated with an amine in a suitable solvent such as toluene, dioxane or dimethylformamide to effect condensation. Specific illustrations for the preparation of these ketones are more fully disclosed in Ser. No. 97,379, filed Dec. 11, 1970, now U.S. Pat. No. 3,859,286, and Ser. No. 137,055, filed Apr. 23, 1971, now U.S. Pat. No. 3,856,789.

Treatment of the 2,7-bis-basic ketones of xanthene and thioxanthene (II) with a reducing agent results in a reduction of the α-carbonyl to form the compounds of the present invention, i.e., the 2,7-bis basic alkanols of xanthene and thioxanthene (I). In general, the reduction is accomplished in a suitable solvent using sodium borohydride as a reducing agent at temperatures which range from about −20° to about 100° C., for periods of time which range anywhere from about 30 minutes to about 24 hours. A variety of solvents can be suitably employed, including tetrahydrofuran, methanol, ethanol and water. When using aqueous or methanolic solutions, a base such as sodium hydroxide is utilized in order to minimize the rate at which the sodium borohydride reagent decomposes. Preferably, the reduction of the 2,7-bis basic ketones of xanthene and thioxanthene is accomplished by dissolving the ketones in tetrahydrofuran and adding solid sodium borohydride in small increments with continued stirring. As a matter of convenience, ice bath temperatures are usually employed with stirring being continued for an additional period of from 1 to 12 hours.

In compounds of the present invention are useful as chemical intermediates for the preparation of the 2,7-bis basic vinylene derivatives of xanthene and thioxanthene, which are disclosed and claimed in copending application Ser. No. 317,128, now U.S. Pat. No. 3,817,992 filed concurrently herewith. These vinylene derivatives are readily prepared by the dehydration of the 2,7-bis basic alkanols of xanthene and thioxanthene under acidic conditions to form the corresponding olefinic derivatives. Dehydration occurs readily under a variety of conditions with a number of dehydrating agents. Thus, for example, 2,7-bis(4-piperidino-1-butenyl)xanthene is prepared by heating an ethylene glycol monoethyl ether solution of α,α'-bis(3-piperidinopropyl)xanthene-2,7-dimethanol in the presence of concentrated hydrochloric acid.

Both the compounds of the present invention as well as the 2,7-bis-basic vinylene derivatives prepared therefrom possess antiviral activity and are useful in inactivating or inhibiting a wide spectrum of viruses by their administration to either an infected or to a non-infected host. Preferably they are administered to an animal host to prevent or inhibit viral infections. The term host refers to any viable biological material or intact animal including humans which is capable of inducing the formation of interferon and which serves as a support means for virus replication. The host can be of animal or mammalian origin. Illustratively such hosts include birds, mice, rats, guinea pigs, gerbils, ferrets, dogs, cats, cows, horses and humans. Other viable biological material such as used in the production of vaccines may also act as a host. Thus, tissue cultures prepared from organ tissues, such as mammalian kidney or lung tissue, as well as tissue cultures prepared from embryo tissue, such as obtained from amniotic cells or chick allantoic fluid, have been found to be useful hosts.

The treatment of virus infections for purposes of the present invention encompasses both the prevention and the inhibition of characteristic disease symptoms in a mammalian host susceptible to invasion by a pathogenic virus. Illustrative of mammalian virus infections which can be prevented or inhibited by the administration of the compounds of the present invention are infections caused by picornaviruses, such as encephalomyocarditis virus; myxoviruses, such as influenza $A_2$ (Jap/305) virus; arboviruses, such as Semliki forest virus; the herpes group of viruses, including herpes simplex; and the poxviruses, as for example vaccinia IHD. Thus, for example, the compounds of the present invention when administered orally or subcutaneously to mice in varying doses either shortly prior or subsequent to a fatal inoculation of a neurotropic virus such as encephalomyocarditis virus, having a $LD_{50}$ anywhere from 5 to 50, delay or prevent completely the onset of death. Salts of these compounds are generally administered in compositions containing a 0.15% aqueous hydroxyethylcellulose vehicle, whereas the free base compounds are generally administered in compositions containing a 10% aqueous surfactant vehicle in order to help solubilize the compound. In general, ten mice are used for each treated group with an additional 20 mice serving as a control group. At the time of administration the test virus is titrated in order to determine the potency or $LD_{50}$ for the particular virus pool used as a challenge. The control animals are given a placebo containing the identical volume of vehicle without, of course, the active ingredient. Because of the lethal nature of the test system employed, the anti-viral nature of the test compound is dramatically illustrated by a side by side comparison of the survival time of treated animals with the untreated control group of animals.

Respiratory viruses, such as influenza $A_2$ (Jap/305) virus, which are also lethal to the test animals employed, are administered via intranasal instillation. Animals infected in this manner have the active ingredients administered in the same manner as the test virus, and again a side by side comparison is made of the survivors of the animals treated with the untreated control animals.

Inexplicably, a mouse fatally infected with encephalomyocarditis or influenza virus occasionally survives without further treatment. This may be the result of a prior, interferon-induced infection in the mouse, or perhaps due to some genetic factor or other natural defense mechanism not presently understood. For this reason the control group selected is of sufficient size as to statistically reduce to a negligible amount the influence of such a chance survivor upon the test results.

The vaccinia test virus is typical of the dermatotrophic type viruses which respond to treatment with compositions containing the compounds of the instant invention. The vaccinia virus generally produces a non-fatal infection in mice, producing characteristic tail lesions when the virus is subcutaneously administered to the tail of the mouse. The instant compounds are administered either orally or subcutaneously either prior to or subsequent to the vaccinia infection. Tail lesions are subjectively scored on the eighth day following infection against untreated animals which serve as a control group. The compounds of the present invention have been found to be effective in varying degrees against one or all of these test virus systems.

The mode of activity of the active ingredients of the present invention is not rigorously defined. Inter alia, the compounds of the present invention may induce the formation of interferon in a viable host. Interferon is a biological substance of unknown chemical structure, presumably proteinaceous in nature, which is produced by host cells in response to a viral infection. The interferon so produced acts to induce a virus inhibiting substance, which inhibits in some yet unknown manner the intracellular replication of the virus without appearing to have any inactivation effect per se upon the virus itself. A few of the viruses susceptible to interferon replication inhibition are described in Horsfall and Tamm, "Viral and Rickettsial Infections of Man" 4th Edition (1965), J. B. Lippincott Company, pp. 328-9.

As previously indicated, the compounds of the present invention may be prophylactically administered in order to prevent the spread of contagious viral diseases or they may be therapeutically administered to a host already infected intended for their curative effect. When administered prophylactically, it is preferred that the administration be made within 0 to 96 hours prior to the infection of the host animal with a pathogenic virus. When the compounds of the present invention are administered for their curative effect, it is preferred that they are administered within about 1 or 2 days following infection of the host in order to obtain the maximum therapeutic effect.

The dosage to be administered will be dependent upon such parameters as the particular virus for which either treatment or prophylaxis is desired, the species of animal involved, its age, health, weight, the extent of infection, concurrent treatment, if any, frequency of treatment and the nature of the effect desired. A daily dose of the active ingredients will generally range from about 0.1 mg to about 500 mg per kg of body weight. Illustratively, dosage levels of the administered active ingredients for intravenous treatment range from about 0.1 mg to about 10 mg per kg of body weight; for intraperitoneal administration range from about 0.1 mg to about 50 mg per kg of body weight; for subcutaneous administration range from about 0.1 mg to about 250 mg per kg of body weight; for oral administration may be from about 0.1 mg to about 500 mg per kg of body weight; for intranasal instillation range from about 0.1 mg to about 10 mg per kg of body weight; and for aerosol inhalation therapy, the range is generally from about 0.1 mg to about 10 mg per kg of body weight.

The novel compounds described herein can also be administered in various different dosage unit forms, e.g., oral compositions such as tablets, capsules, dragees, lozenges, elixirs, emulsions, clear liquid solutions and suspensions; parenteral compositions such as intramuscular, intravenous or intradermal preparations; and topical compositions, such as lotions, creams or ointments. The amount of active ingredient contained in each dosage unit form will, of course, vary widely according to the particular dosage unit employed, the animal host being treated, and the nature of the treatment, i.e., whether prophylactic or therapeutic in nature. Thus, a particular dosage unit may contain from about 2.0 mg to over 3.0 g of active ingredient in addition to the pharmaceutical excipients contained therein.

The novel compounds described herein can be employed in conjunction or admixture with additional organic or inorganic pharmaceutical excipients. Suitable solid excipients include gelatin, lactose, starches, magnesium stearate and petrolatum. Suitable liquid excipients include water and alcohols such as ethanol, benzyl alcohol and the polyethylene alcohols either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5% to about 25% by weight, and preferably from about 1% to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil.

A suitable method of administration for the compounds of the present invention is orally either in a solid dose form such as a tablet or capsule, or in a liquid dose form such as an elixir, suspension, emulsion or syrup. Ordinarily the active ingredient comprises from about 0.5% to about 10% by weight of an oral liquid composition. In such compositions, the pharmaceutical carrier is generally aqueous in nature, as for example, aromatic water, a sugar-based syrup or a pharmaceutical mucilage. For insoluble compounds suspending agents may be added as well as agents to control viscosity, as for example, magnesium aluminum silicate or carboxymethylcellulose. Buffers, preservatives, emulsifying agents and other excipients can also be added.

For parenteral administration such as intramuscular, intravenous or subcutaneous administration, the proportion of active ingredient ranges from about 0.05% to about 20% by weight, and preferably from about 0.1% to about 10% by weight of the liquid composition. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 0.05% to about 20% by weight of the total formulation, the remaining component or components comprising liquid pharmacuetical excipients previously mentioned.

The active ingredients of the present invention can also be admixed directly with animal feeds or incorporated into the drinking water of animals. For most purposes, an amount of active ingredient is used which provides from about 0.0001% to about 0.1% and preferably, from about 0.001% to about 0.02% by weight of the active ingredient based upon the total weight of feed intake. The active ingredients can be admixed in animal feed concentrates, suitable for use by farmers or livestock growers for incorporation in appropriate amounts with the final animal feeds. These concentrates ordinarily comprise from about 0.5% to about 95% by weight of the active ingredient compounded with a finely divided solid carrier or flour, such as wheat, corn, soybean or cottonseed flour. Depending upon the particular animal to be fed, nutrients and fillers may also be added such as ground cereal, charcoal, fuller's earth, oyster shells and finely divided attapulgite or bentonite.

The active ingredients of the present invention can be packaged in a suitable pressurized container together with an aqueous or volatile propellant for use as an aerosol. A suitable discharge valve is fitted to an opening in the container from which the active ingredients may be conveniently dispensed in the form of a spray, liquid, ointment or foam. Additional adjuvants such as co-solvents, wetting agents and bactericides may be employed as necessary. Normally, the propellant used is a liquified gaseous compound, preferably a mixture of low molecular weight fluorinated hydrocarbons. These haloalkanes are preferred because of their compatibility with the active ingredients of the present invention, and because they are non-irritating when applied to skin surfaces. Other useful propellants include ethylene oxide, carbon dioxide, propane and nitrogen gas.

The invention described herein is more particularly illustrated by means of the following specific examples:

EXAMPLE I 2,7-Bis(4-chlorobutyryl)xanthene

To a mixture of 91.1 g (0.5 mole) of xanthene, 176.3 g (1.25 moles) of 4-chlorobutyryl chloride and 3 liters of dry methylene chloride, chilled to −20° C., is slowly added over a 30 minute period 146.7 g (1.1 moles) of aluminum chloride, during which the temperature is maintained below −10° C. Following the addition, the reaction temperature is slowly permitted to rise to room temperature and then refluxed for an additional 4 hours. Upon cooling, the mixture is decomposed by cautiously pouring into 2 liters of an ice-water mixture. The liquid layers are separated and the aqueous layer extracted with methylene chloride. The combined organic layers are evaporated to a small volume and cooled. The resulting 2,7-bis(4-chlorobutyryl)xanthene so obtained is recrystallized from acetone to yield the desired product having a m.p. 131°–2° C.

EXAMPLE II 2,7-Bis(3-chloropropionyl)thioxanthene

To a mixture of 99.2 g (0.5 mole) of thioxanthene, 158.5 g (1.25 mole) of 3-chloropropionyl chloride, and 3 liters of previously dried methylene chloride, chilled to −20° C., is slowly added 146.7 g (1.1 mole) of aluminum chloride over a 30 minute period while maintaining the temperature at below −10° C. Following the addition of aluminum chloride the reaction mixture is slowly permitted to rise to room temperature and then refluxed for an additional 4 hours. The reaction mixture is cooled to room temperature and decomposed by cautiously pouring into 2 liters of an ice-water mixture. The liquid layers are separated and the aqueous layer re-extracted with methylene chloride. The combined organic layers are evaporated to a small volume and cooled. The desired 2,7-bis(3-chloropropionyl)thioxanthene which separates on standing is recrystallized from acetone to yield the desired product having a m.p. of 175°–7° C.

EXAMPLE III 2,7-Bis(4-piperidinobutyryl)xanthene

A mixture of 19.6 (0.05 mole) of 2,7-bis(4-chlorobutyryl)xanthene, 34.0 g (0.4 mole) of piperidine, 16.6 g (0.1 mole) of potassium iodide and 200 ml of butanone is refluxed with stirring for a period of 60 hours. The reaction mixture is cooled and poured into 1 liter of water. The solid which precipitates is filtered, crystallized from a methyl chloride-acetone solution and again recrystallized from acetone to yeild the desired 2,7-bis(4-piperidinobutyryl)xanthene having a m.p. of 115°–7° C.

EXAMPLE IV 2,7-Bis[3-(diethylamino)propionyl]thioxanthene dihydrochloride dihydrate A mixture of 13.0 g (0.034 mole) of 2,7-bis(3-chloropropionyl)thioxanthene, 1 g of potassium iodide, 75 ml of diethylamine and 75 ml of tetrahydrofuran is permitted to stand at room temperature for a period of 72 hours and filtered. The residue is thoroughly washed with tetrahydrofuran and the combined filtrate is evaporated to dryness. The residue so obtained is dissolved in a minimum of ethanol, treated with ethanolic HCl to form the dihydrochloride salt and diluted with diethyl ether. The product which forms is filtered, crystallized from a methanol-diethyl ether solution and hydrated in a constant humidity chamber to give the desired 2,7-bis[3-(diethylamino)propionyl]thioxanthene as the dihydrochloride dihydrate having a m.p. of 137°–40° C.

EXAMPLE V

α,α'-Bis(3-piperidinopropyl)xanthene -2,7-dimethanol

To a cooled, stirred solution of 25.6 g (0.053 moles) of 2,7-bis(4-piperidinobutyryl)xanthene dissolved in 200 ml of tetrahydrofuran is added a solution of 4.2 g (0.11 moles) of sodium borohydride contained in a solution of 50 ml of methanol and 5 ml of a 10% sodium hydroxide solution. The resulting mixture is allowed to warm gradually to room temperature and stirring continued overnight. The reaction mixture is diluted with water and the solid which forms is filtered, washed with water and air dried. The solid product is dissolved in a 10% hydrochloric acid solution, filtered and the filtrate made alkaline with a 10% sodium hydroxide solution. The alkaline filtrate is extracted with methylene chloride. The organic extract is then washed with water, followed by a wash of saturated sodium chloride solution, dried over anhydrous magnesium sulfate, filtered and evaporated to dryness in vacuo. The residue containing the desired α,α'-bis(3-piperidinopropyl)xanthene-2,7-dimethanol is recrystallized twice from benzene to yield a product having a m.p. of 145°–6° C.

Following essentially the same procedure, but substituting: 2,7-bis[4-(diethylamino)butyryl]xanthene, 2,7-bis[4-(diallylamino)butyryl]xanthene, 2,7-bis[3-(diethylamino)propionyl]xanthene, 2,7-bis[4-(diethylamino) butyryl]thioxanthene, 2,7-bis(4-piperidinobutyryl)thioxanthene or 2,7-bis[3-(dimethylamino)propionyl]thioxanthene for the 2,7-bis(4-piperidinobutyryl)xanthene above, results in the formation of α,α'-bis[3-(diethylamino)propyl]xanthene-2,7-dimethanol, α,α'-bis[3-(diallylamino)propyl]xanthene-2,7-dimethanol, α,α'-bis[2-(diethylamino)ethyl]xanthene-2,7-dimethanol, α,α'-bis[3-(diethylamino)propyl]thioxanthene-2,7-dimethanol, α,α'-bis(3-piperidinopropyl)thioxanthene-2,7-dimethanol and α,α'-bis[2-(dimethylamino)ethyl]thioxanthene-2,7-dimethanol, respectively.

EXAMPLE VI

The following Example is illustrative of the antiviral activity for the compounds of the present invention.

Thirty mice each weighing approximately 10 to 12 gms are divided into two groups, a control group containing 20 animals and a test group of 10 animals. All of the animals are challenged with a fatal dose ($5LD_{50}$) of encephalomyocardit is virus. The test group of animals are treated both prophylactically and therapeutically using a parenteral composition containing α,α'-bis(3-piperidinopropyl)xanthene-2,7-dimethanol as the active ingredient dissolved in a 10% solution of sorbitan monooleate. The composition contains the active ingredient in an amount such that each dosage contains 0.25 ml which is equivalent to a dose level of 50 mg per kg. The control group receives a subcutaneous placebo containing the same volume of vehicle without, of course, the active ingredient. Observations over a ten day period show a termination of all the control animals within a period of from 4 to 5 days, with the treated group of animals surviving for a statistically longer period of time.

In a similar manner another group of 30 mice weighing approximately 20 gms each are divided into two groups, a control group of 20 animals and a test group of 10 animals. All of the animals are challenged with a fatal dose ($5LD_{50}$) of influenza $A_2$ (Jap/305) virus via intranasal instillation. Prophylactic treatment consists of the administration of α,α'-bis(3-piperidinopropyl)xanthene-2,7-dimethanol dissolved in a 10% solution of sorbitan monooleate 24 hours prior to infection. The composition contains the active ingredient in an amount such that each dosage unit contains an equivalent dose level of 100 mg per kg. The control group receives an intranasal placebo containing the same volume of vehicle without, of course, the active ingredient. Observations over a 10 day period show the termination of all the control animals within a period of from about 7 days, with the treated group of animals surviving the fatal challenge of influenza virus for a statistically greater period of time.

EXAMPLE VII

Preparation of a capsule formulation

An illustrative composition for hard gelatin capsules is as follows:

| | | Per Capsule |
|---|---|---|
| (a) | α,α'-bis[3-(dimethylamino)propyl] xanthene-2,7-dimethanol dihydrochloride | 200 mg |
| (b) | Talc | 35 mg |

The formulation is prepared by passing the dry powders of both (a) and (b) through a fine mesh screen and mixing them well. The powder is then filled into No. 0 hard gelatin capsules at a net fill of 235 mg per capsule.

In a similar fashion, a soft gelatin capsule is prepared in which the talc is omitted. The dry α,α'-bis[3-(dimethylamino)propyl]xanthene-2,7-dimethanol dihydrochloride powder can be filled as a granulation, slug or compressed tablet directly into the rotary dye or plate mold in which the soft gelatin capsule is formed.

EXAMPLE VIII

Preparation of a tablet formulation

An illustrative composition for tablets is as follows:

| | | Per Tablet |
|---|---|---|
| (a) | α,α'-bis(3-piperidinopropyl) xanthene-2,7-dimethanol dihydrochloride | 100 mg |
| (b) | Wheat starch and starch paste | 15 mg |
| (c) | Lactose | 33.5 mg |
| (d) | Magnesium stearate | 1.5 mg |

The granulation obtained upon mixing lactose starch and granulated starch paste is dried, screened and mixed with the active ingredient and magnesium stearate. The mixture is compressed into tablets weighing 150 milligrams each.

EXAMPLE IX

Preparation of an oral syrup formulation

A 2% weight per volume syrup of α,α'-bis[3-(diethylamino)propyl]xanthene-2,7-dimethanol dihydrochloride is prepared by the usual pharmaceutical techniques in accordance with the following formula:

|     |                                              | Grams |
|-----|----------------------------------------------|-------|
| (a) | α,α'-bis[3-(diethylamino)propyl]xanthene-2,7-dimethanol dihydrochloride | 2.0 |
| (b) | Sucrose                                      | 33.3  |
| (c) | Chloroform                                   | 0.25  |
| (d) | Sodium benzoate                              | 0.4   |
| (e) | Methyl p-hydroxybenzoate                     | 0.02  |
| (f) | Vanillin                                     | 0.04  |
| (g) | Glycerol                                     | 1.5   |
| (h) | Purified water to 100.0 ml                   |       |

EXAMPLE X

Preparation of parenteral formulation

An illustrative composition for a parenteral injection is the following emulsion:

| Each ml Contains | Ingredient | Amount |
|---|---|---|
| 50 mg | α,α'-bis[3-(diethylamino)propyl]xanthene-2,7-dimethanol | 1.000 g |
| 100 mg | Polyoxyethylene sorbitan monooleate | 2.000 g |
| 0.0064 | Sodium chloride | 0.128 g |
|  | Water for injection, q.s. | 20.000 ml |

The parenteral composition is prepared by dissolving 0.64 g of sodium chloride in 100 ml of water for injection, mixing the polyoxyethylene sorbitan monooleate with the α,α'-bis[3-(diethylamino)propyl]xanthene-2,7-dimethanol, adding a sufficient solution of the sodium chloride in water to the active ingredient and polyoxyethylene sorbitan monooleate to make 20 ml, shaking the mixture, and then autoclaving the mixture for 20 minutes at 110° C. at 15 p.s.i.g. steam pressure. The composition can be dispensed in a single ampule for multiple dosage or in 10 or 20 ampules for single dosages.

EXAMPLE XI

Preparation of dusting powder formulation

The following formulation illustrates a dusting powder for topical use:

|     |                                              | Per Kilogram |
|-----|----------------------------------------------|--------------|
| (a) | α,α'-bis[2-(diethylamino)ethyl]thioxanthene-2,7-dimethanol dihydrochloride | 20 gm |
| (b) | Silica aerogel | 980 gm |

The dusting powder is prepared by intimately blending the ingredients. The resulting mixture is then packaged in suitable dispensing containers.

We claim:

1. A 2,7-bis basic alkanol derivative of xanthene and thioxanthene having the general formula:

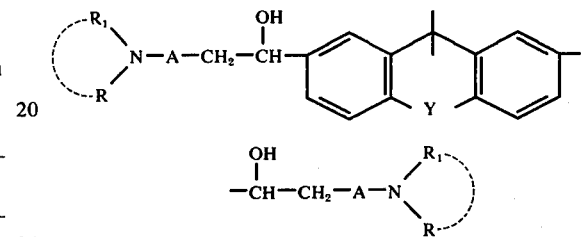

wherein Y is oxygen or sulfur; A is a straight or branched alkylene chain having from 1 to 4 carbon atoms; R and $R_1$ are each selected from the group consisting of, lower alkyl having from 1 to 6 carbon atoms, cycloalkyl having from 3 to 6 carbon atoms, alkenyl having from 3 to 6 carbon atoms in which the unsaturation is in a position other than in the 1-position of the alkenyl group, and when R and $R_1$ are taken together with the nitrogen atom to which they are attached represent the pyrrolidinyl, morpholino or piperidino radical; and the pharmaceutically acceptable acid addition salts thereof.

2. A compound of claim 1 wherein each R and $R_1$ is a lower alkyl group having from 1 to 6 carbon atoms.

3. The compound α,α'-bis(3-piperidinopropyl)xanthene-2,7-dimethanol and the pharmaceutically acceptable acid addition salts thereof.

4. The compound α,α'-bis[3-(diethylamino)propyl]xanthene-2,7-dimethanol and the pharmaceutically acceptable acid addition salts thereof.

5. The compound α,α'-bis[3-(dimethylamino)propyl]thioxanthene-2,7-dimethanol and their pharmaceutically acceptable acid addition salts thereof.

* * * * *